(12) United States Patent
Ziemer et al.

(10) Patent No.: US 7,098,169 B2
(45) Date of Patent: Aug. 29, 2006

(54) HERBICIDE-SAFENER COMBINATION BASED ON ISOXAZOLINE CARBOXYLATE SAFENERS

(75) Inventors: Frank Ziemer, Kriftel (DE); Lothar Willms, Hofheim (DE); Christopher Rosinger, Hofheim (DE); Erwin Hacker, Hochheim (DE); Hermann Bieringer, Eppstein (DE); Ken Pallett, Königstein (DE)

(73) Assignee: Bayer CropScience GmbH, Frankfurt am Main (DE)

( * ) Notice: Subject to any disclaimer, the term of this patent is extended or adjusted under 35 U.S.C. 154(b) by 0 days.

(21) Appl. No.: 11/093,658

(22) Filed: Mar. 29, 2005

(65) Prior Publication Data

US 2005/0170963 A1    Aug. 4, 2005

Related U.S. Application Data

(63) Continuation of application No. 10/470,509, filed as application No. PCT/EP02/01002 on Jan. 31, 2002, now abandoned.

(30) Foreign Application Priority Data

Jan. 31, 2001    (EP)    .................... 01102222

(51) Int. Cl.
*A01N 25/32*    (2006.01)
*A01P 13/00*    (2006.01)

(52) U.S. Cl. .................. 504/106; 504/108; 504/271

(58) Field of Classification Search ........... 504/106, 504/108, 271
See application file for complete search history.

(56) References Cited

U.S. PATENT DOCUMENTS 5,516,750 A    5/1996    Willms et al.
5,536,698 A    7/1996    Loeher et al.
6,124,240 A    9/2000    Bieringer et al.

FOREIGN PATENT DOCUMENTS

| WO | WO 00/03591 |    | 1/2000 |
| WO | WO 00/08932 |    | 2/2000 |
| WO | WO 00/30447 |    | 6/2000 |
| WO | WO 01/17350 | A1 | 3/2001 |
| WO | WO 01/22819 | A1 | 4/2001 |
| WO | WO 01/24633 | A2 | 4/2001 |
| WO | WO 01/35740 | A2 | 5/2001 |
| WO | WO 01/37652 | A2 | 5/2001 |

*Primary Examiner*—S. Mark Clardy
(74) *Attorney, Agent, or Firm*—Frommer Lawrence & Haug LLP

(57) ABSTRACT

Herbicide safener combiantions consisting of A) an effective amount of a compound of the formula (1) or a salt thereof, in which $R^1$ is phenyl which is unsubstituted or substituted, $R^2$ is $(C_1–C_6)$alkyl, $(C_3–C_6)$cycloalkyl or phenyl, each of the 3 last-mentioned radicals is unsubstituted or substituted, $R^3$ is hydrogen or a hydrocarbon radical having 1 to 18 C-atoms which is unsubstituted or substituted, and B) a herbicide selected form the group consisting of and florasulam, chloransulam, dicamba, diflufenzopyr; triclopyr, fluroxypyr, metribuzin, carfentrazone-ethyl, S.metolachlor, dimethenamide, dimethenamide-P or flufenacet and mixtures of the above herbicides, optionally in combination with herbicidal active ingredients, can be used for effective selective controlling weeds in crop such as maize

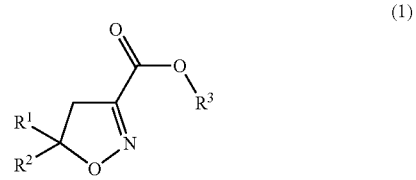

(1)

31 Claims, No Drawings

HERBICIDE-SAFENER COMBINATION BASED ON ISOXAZOLINE CARBOXYLATE SAFENERS

This application is continuation application of U.S. application Ser. No. 10/470,509, filed on 29 Jul. 2003, now abandoned, which is a National Phase application filed under 35 U.S.C. § 371 of PCT/EP002/01002, filed on Jan. 31, 2002 (now WO 02/060255).

The present invention relates to the safening of crop plants against damage of herbicidal compounds occurring while using the pesticides for controlling undesired organisms in crops or useful plants including ornamental plants. The invention more particularly relates to the use of 5,5-diphenyl-2-isoxazoline-3-carboxylic acid derivatives as safeners for different herbicides and novel herbicide-safener compositions.

U.S. Pat. No. 5,516,750 describes the use of substituted isoxazolines as safeners for different classes of pesticides, especially for post-emergent (tankmix) application of a safener-herbicide combination to the area-under cultivation. . .

It is further known from DE-A-19853827 (WO-A-00/30447) that isoxazoline safeners are specifically useful for safening crops from damage of various herbicides from the group of p-hydroxyphenyl pyruvate dioxygenase inhibitors (HPPDO inhibitors) such as sulcotrione, mesotrione or isoxaflutole, wherein the safener in the disclosed examples is applied pre- or post-emergence together with the herbicide.

It has now been found that compounds from the group of 2-isoxazoline-3-carboxylic acid derivatives of the formula (I) below can be used effectively as a safeners for specific herbicides in crops of useful plants, preferably corn.

The invention thus relates to a novel herbicide safener combination consisting of A) an effective safening amount of a compound of the formula (I) or a salt thereof,

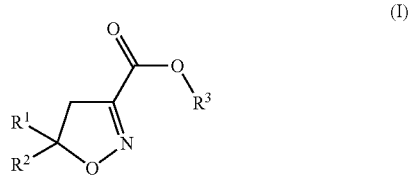

(I)

in which $R^1$ is phenyl which is unsubstituted or substituted, preferably unsubstituted or substituted by one or more radicals selected from the group consisting of halogen, cyano, nitro, amino, $(C_1-C_4)$haloalkyl, $(C_1-C_4)$haloalkoxy, $(C_1-C_4)$alkyl, $(C_1-C_4)$alkoxy, mono$(C_1-C_4)$alkyl-amino, di$(C_1-C_4)$alkyl-amino, $(C_1-C_4)$alkylthio and/or $(C_1-C_4)$alkylsulfonyl, $R^2$ is $(C_1-C_6)$alkyl, $(C_3-C_6)$cycloalkyl or phenyl, each of the 3 last-mentioned radicals is unsubstituted or substituted, preferably unsubstituted or substituted by one or more radicals selected from the group consisting of halogen, cyano, nitro, amino, $(C_1-C_4)$haloalkyl, $(C_1-C_4)$haloalkoxy, $(C_1-C_4)$alkyl, $(C_1-C_4)$alkoxy, mono$(C_1-C_4)$alkyl-amino, di$(C_1-C_4)$alkyl-amino, $(C_1-C_4)$alkylthio and/or $(C_1-C_4)$alkylsulfonyl, $R^3$ is hydrogen or a hydrocarbon radical having 1 to 18 C-atoms which is unsubstituted or substituted, preferably unsubstituted or substituted by one or more radicals selected from the group consisting of
  halogen, cyano, thio, nitro, hydroxyl, $(C_1-C_6)$alkyl, $(C_1-C_6)$haloalkyl, the 2 last-mentioned radicals as substituents of cyclic radicals only, $(C_1-C_6)$alkoxy, $(C_2-C_6)$alkenyloxy, $(C_2-C_6)$alkinyloxy, $(C_1-C_6)$haloalkoxy, $(C_2-C_6)$alkylthio, $(C_3-C_6)$cycloalkyl, $(C_3-C_6)$cycloalkoxy, $(C_1-C_8)$alkoxy-carbonyl, $(C_2-C_6)$alkenyloxy-carbonyl, $(C_2-C_6)$alkinyloxy-carbonyl, $(C_1-C_8)$alkyl-carbonyl, $(C_1-C_6)$alkyl-carbonyloxy, phenyl, phenyl-$(C_1-C_6)$alkoxy, phenyl-$(C_1-C_6)$alkoxy-carbonyl, phenoxy, phenoxy-$(C_1-C_6)$alkoxy, phenoxy-$(C_1-C_6)$alkoxy-carbonyl, phenoxycarbonyl, phenylcarbonyloxy and phenyl-$(C_1-C_6)$alkyl-carbonyloxy,
    wherein the 9 last-mentioned radicals are unsubstituted or substituted in the phenyl ring, preferably unsubstituted or substituted by one or more radicals selected from the group consisting of halogen, $(C_1-C_4)$alkyl, $(C_1-C_4)$alkoxy, $(C_1-C_4)$haloalkyl, $(C_1-C_4)$haloalkoxy and nitro,
  and radicals of the formula —O—N=CR'$_2$, —N=CR'$_2$,
    wherein the R' in the formulae independently of one another are hydrogen, $(C_1-C_4)$alkyl or phenyl, which is unsubstituted or substituted by one or more radicals selected from the group consisting of halogen, $(C_1-C_4)$alkyl, $(C_1-C_4)$alkoxy, $(C_1-C_4)$haloalkyl, $(C_1-C_4)$haloalkoxy and nitro, or together are a $(C_2-C_6)$alkylene chain, and B) a herbicide selected from the group consisting of
  (B1) Triazolopyrimidine derivatives (B1-1) and (B1-2)
  (B1-1) N-(2,6difluorophenyl)-8-fluoro-5-methoxy-1,2,4-triazolo[1,5-c]pyrimidin-2-sulfonamide (florasulam),
  (B-1-2) methyl 3-chloro-(5-ethoxy-7-fluoro[1,2,4]triazole-[1,5-c]pyrimidin-2-ylsulfonamido)-benzoate (chloransulam)
  (B2) plant hormone-type herbicides (B2-1) to (B2-4)
  (B2-1) 3,6-dichloro-2-methoxy-benzoic acid and salts and esters (e. g. methyl ester) thereof; (dicamba),
  (B2-2) 2-{1-[4-(3,5-difluorophenyl)semicarbazono]ethyl}nicotinic acid and salts (e. g. sodium salty thereof (diflufenzopyr);
  (B2-3) 3,5,6-trichloro-2-pyridyloxyacetic acid (triclopyr);
  (B2-4) 4-amino-3,5-dichloro-6-fluoro-2-pyridyloxyacetic acid and salts and esters thereof (fluroxypyr); and
  (B3-1) 4-amino-6-tert-butyl-4,5-dihydro3-methylthio-1,2,4-triazin-5-one (metribuzin);
  (B4-1) ethyl (RS)-2-chloro-3-[2-chloro-5-(4-difluoromethyl-4,5-dihydro-3-methyl-5-oxo-1H-1,2,4-triazol-1-yl)-4-fluorophenyl]propionate (carfentrazone-ethyl)
  (B5) chloroacetanilides (B5-1) to (B5-4)
  (B5-1) 2-chloro-N-(2-ethyl-6-methylphenyl)-N-[(1S)-2-methoxy-1-methylethyl)]-acetamide (S-metolachlor),
  (B5-2) (RS)-2-chloro-N-(2,4-diethyl-3-thienyl)-N-(2-methoxy-1-methylethyl)acetamide (dimethenamide),
  (B5-3) (S)-2-chloro-N-(2,4-diethyl-3-thienyl)-N-(2-methoxy-1-methylethyl)acetamide (dimethenamide-P), and
  (B5-4) 4'-fluoro-N-isopropyl-2-[5-trifluoromethyl-1,3,4-thiadiazol-2-yloxy]acetanilide (flufenacet) and mixtures of the above herbicides, optionally in combination with other herbicidal active ingredients.

The terms in the formulae mentioned hereinabove and hereinbelow have the meanings outlined below:

A "hydrocarbon radical" is a straight-chain, branched or cyclic hydrocarbon radical which may be saturated, partially saturated, unsaturated or aromatic, for example alkyl, alkenyl, alkynyl, cycloalkyl, cycloalkenyl and aryl, preferably alkyl, alkenyl and alkynyl having up to 18 carbon atoms, preferably 12 carbon atoms, particularly 6 C-atoms, or cycloalkyl having 3 to 6 ring atoms or phenyl.

In the cases where two or more radicals are selected from a group of radicals as substituents at the same basic radical these radicals may be identical or different.

The term "halogen" includes fluorine, chlorine, bromine and iodine.

The term "$(C_1-C_4)$alkyl" is to be understood as a straight-chain or branched hydrocarbon radical having 1, 2, 3 or 4 carbon atoms, for example the methyl, ethyl, propyl, isopropyl, 1-butyl, 2-butyl, 2-methylpropyl-or tert-butyl radical. Correspondingly, alkyl radicals having a greater range of carbon atoms are to be understood as straight-chain or branched saturated hydrocarbon radicals which contain a number of carbon atoms which corresponds to this range. The term "$(C_1-C_6)$alkyl" thus includes the abovementioned alkyl radicals, and also, for example, the pentyl, 2-methylbutyl, 1,1-dimethylpropyl and hexyl radical. In alkyl radicals or moieties throughout the definitions of radicals and composite radicals the number of carbon atoms is preferably from 1 to 4 unless otherwise defined more narrowly.

"$(C_1-C_4)$haloalkyl" is to be understood as an alkyl group mentioned under the term "$(C_1-C_4)$alkyl" in which one or more hydrogen atoms are replaced by the corresponding number of identical or different halogen atoms, preferably chlorine or fluorine, such as the trifluoromethyl, the 1-fluoroethyl, the 2,2,2-trifluoroethyl, the chloromethyl, fluoromethyl, the difluoromethyl and the 1,1,2,2-tetrafluoroethyl group.

"$(C_1-C_4)$alkoxy" is to be understood as an alkoxy group whose hydrocarbon radical has the meaning given under the term "$(C_1-C_4)$alkyl". Alkoxy groups embracing a larger range of carbon atoms are to be understood likewise.

The terms "alkenyl" and "alkynyl" having a prefix stating a range of carbon atoms denote a straight-chain or branched hydrocarbon radical having a number of carbon atoms corresponding to this range, this hydrocarbon radical having at least one multiple bond which can be in any position of the unsaturated radical in question. "$(C_2-C_6)$alkenyl" thus denotes, for example, the vinyl, allyl2-methyl-2-propenyl, 2-butenyl, pentenyl, 2-methylpentenyl or the hexenyl group. "$(C_2-C_6)$-alkynyl" denotes, for example, the ethinyl, propargyl, 2-methyl-2-propinyl, 2-butinyl, 2-pentinyl or the 2-hexinyl group.

"$(C_3-C_6)$cycloalkyl" denotes monocyclic alkyl radicals, such as the cyclopropyl, cyclobutyl, cyclopentyl or cyclohexyl radical.

Other composite terms, such as $(C_1-C_6)$alkylthio, $(C_1-C_6)$alkylsulfonyl $(C_3-C_6)$cycloalkenyl or $[(C_1-C_6)$alkoxy]carbonyl are to be understood correspondingly, in accordance with the above definitions.

It will be understood that the use of salts of the safeners of formula (I), preferably salts formed by compounds when $R^3$ is hydrogen, is also embraced by the invention.

The compounds of the formula (I) can form salts. Salt formation may occur by action of a base on those compounds of the formula (I) which carry an acidic hydrogen atom, for example those compounds (I) in which $R^3$ is hydrogen. Suitable bases are, for example, organic amines and also ammonium, alkali metal or alkaline earth metal hydroxides, carbonates and bicarbonates, in particular sodium hydroxide and potassium hydroxide, sodium carbonate and potassium carbonate and sodium bicarbonate and potassium bicarbonate. Salt formation can also occur by addition of an acid to basic groups, such as amino and alkylamino. Acids which are suitable for this purpose are inorganic and organic acids, for example HCl, HBr, $H_2SO_4$, $HNO_3$ and acetic acid.

Of particular interest are safener compounds of said formula (I) or salts thereof in which $R^1$ and $R^2$ both are phenyl.

Of particular interest are also safener compounds of said formula (I) or salts thereof in which $R^3$ is hydrogen or $(C_1-C_6)$alkyl which is unsubstituted or substituted by one or more radicals selected from the group consisting of halogen, cyano, $(C_1-C_4)$alkoxy, $(C_2-C_4)$alkenyloxy, $(C_2-C_4)$alkinyloxy, $(C_1-C_4)$haloalkoxy, $(C_2-C_4)$alkylthio, $(C_3-C_6)$cycloalkyl, $(C_3-C_6)$cycloalkoxy, $(C_1-C_4)$alkoxy-carbonyl, $(C_2-C_4)$alkenyloxy-carbonyl, $(C_2-C_4)$alkinyloxy-carbonyl, $(C_1-C_4)$alkyl-carbonyl, $(C_1-C_4)$alkyl-carbonyloxy, phenyl which is unsubstituted or substituted in the phenyl ring by one or more radicals selected from the group consisting of halogen, $(C_1-C_4)$alkyl, $(C_1-C_4)$alkoxy, $(C_1-C_4)$haloalkyl and $(C_1-C_4)$haloalkoxy.

Preferred are compounds (I) in which $R^3$ is H or $(C_1-C_4)$ alkyl, specifically hydrogen, methyl or ethyl. Preferred are also salts formed from compounds (I) where $R^3$ is hydrogen.

Preferably the safener of formula (I) is 5,5-diphenyl-2-isoxazoline-3-carboxylic acid (Ia) or ethyl 5,5-diphenyl-2-isoxazoline-3-carboxylate (Ib) (known under the common name isoxadifen or isoxadifen-ethyl, respectively).

The herbicide-safener combinaton can be applied to the plants, seed of the plants, to the locus where the crop and weed plants are growing area under cultivation. The active components of the combination can be applied simultaneously or in sequential order in pre- or postemergence application. In particular the herbicide safener combination can be formulated together and applied together in pre-emergence application or post-emergence application. The components can be formulated separately and applied sequentially. The safener can also be applied to the seeds or other propagation material of the crops prior to sowing or to the soil shortly after sowing in an in furrow-treatment.

The safeners reduce phytotoxic effects of pesticides to the propagation material, seeds, germinated crops of useful plants or to the already emerged crops of useful plants substantially.

The safeners of formula (I) and salts thereof (above and in the following also shortly together "safeners (I)" or "safeners of formula (I)") are capable of reducing or eliminating altogether harmful side effects of these pesticides in crop plants, without adversely affecting the efficacy of these herbicides against weeds. Damage which is caused by using a plurality of herbicides, for example by a plurality of herbicides or by herbicides in combination with insecticides or fungicides, can be reduced significantly or eliminated altogether. Thus, the area of application of conventional pesticides can be widened very considerably.

Additional pesticides which can be combined with the invention combination are for example:

Insecticides which, on their own or together with herbicides, can cause damage to plants include, for example:

organophosphates, for example terbufos (Counter®), fonofos (Dyfonate®), phorate (Thimet®) chlorpyriphos (Reldan®), carbamates, such as carbofuran (Furadan®), pyrethroid insecticides, such as tefluthrin (Force®), deltamethrin (Decis®) and tralomethrin (Scout®) and other insecticidal agents having a different mechanism of action.

Herbicides whose phytotoxic side effects on crop plants can be reduced using compounds of the formula I are, for example, herbicides from the group of the carbamates, thiocarbamates, haloacetanilides, substituted phenoxy-, naphthoxy- and phenoxyphenoxy carboxylic acid derivatives and heteroaryloxyphenoxyalkane carboxylic acid derivatives, such as quinolyloxy-, quinoxalyloxy-, pyridyloxy-, benzoxazolyloxy- and benzothiazolyloxyphenoxyalkane carboxylic acid esters, cyclohexanedione derivatives, imidazolinones, pyrimidinyloxypyridincarboxylic acid derivatives, pyrimidyloxybenzoic acid derivatives, sulfonylureas, triazolopyrimidinesulfonamide derivatives and S-(N-aryl-N-alkylcarbamoylmethyl)dithiophosphoric esters, hormone-type herbicides, pyridinecarboxylic acids, triazinones, triazolinones, pyridinecarboxamides, hydroxybenzonitriles, isoxazoles. Preference is given to phenoxyphenoxy- and heteroaryloxyphenoxy carboxylic acid esters and salts, sulfonylureas, imidazolinones; isoxazoles and herbicides which, together with ALS inhibitors (acetolactate synthetase inhibitors), are employed for widening the activity spectrum, for example bentazone, cyanazin, atrazin, bromoxynil, dicamba and other leaf-acting herbicides.

The herbicides of group B are known, for example, from the above-mentioned publications and from "The Pesticide Manual", The British Crop Protection Council and the Royal Soc. of Chemistry, 12th Edition, 2000, "Agricultural Chemicals Book II—Herbicides—", by W. T. Thompson, Thompson Publications, Fresno Calif., USA 1990 and "Farm Chemicals Handbook '90", Meister Publishing Company, Willoughby Ohio, USA,1990. Other compounds for use in this invention, such as the herbicidal benzoylisoxazole and/or dione compounds as far as not commercially available, may be prepared by the methods described in the aforementioned patent publications, or by the application or adaptation of known methods used or described in the chemical literature for similar compounds.

In some cases the common names are mentioned in the herbicide list. In such case the common name identifies the active ingredient in its commercially available form or forms including derivatives such as salts and esters, even if a specific salt or ester is not mentioned specifically, preferably its usual commercial form.

The safeners of the formula I (a) according to the invention have a particular advantage in combination with herbicides (B). This is because said herbicides cause considerable damage to useful plants, in particular in crops of cereals, in maize and rice, and they can therefore not always be employed in these crops.

The application of the herbicides can be in pre- or post-emergence application. The preferred application method depends on the usual or optimal application time of the particular herbicide or herbicide combination.

Some embodiments of the application, method thus follow the scheme (abbreviation: PE=pre-emergence application,
PO=post-emergence applications, ST=seed treatment):

PE (herbicide+safener)
PO (herbicide+safener)
PE (herbicide 1+herbicide 2+safener)
PO (herbicide 1+herbicide 2+safener)
PE (herbicide 1)+PO (herbicide 2+safener)
PE (herbicide 1+safener)+PO (herbicide 2+safener)
ST (safener)+PO (herbicide)
ST (safener)+PO (herbicide 1+herbicide 2)
ST (safener)+PE (herbicide)
ST (safener)+PE (herbicide+safener)
ST (safener)+PO (herbicide+safener)
ST (safener)+PE (herbicide 1+safener)+PO (herbicide 2+safener)

Preferred example s for the invention method are:
1. Treatment of weeds in corn post-emergent with a combinaton of safener (I), such as (Ia) or (Ib), defined above, and florasulam, chloransulam, dicamba, diflufenzopyr; triclopyr, fluroxypyr, metribuzin, carfentrazone-ethyl, S-metolachlor, dimethenamide, dimethenamide-P or flufenacet.
2. Treatment of weeds in corn post-emergent with a combinaton of safener (I), such as (Ia) or (Ib), defined above, and with combination of dicamba+diflufenzopyr.
3. Treatment of weeds in corn pre-emergent with a combinaton of safener (I), such as (Ia) or (Ib), defined above, and florasulam, chloransulam, dicamba, diflufenzopyr; triclopyr, fluroxypyr, metribuzin, carfentrazone-ethyl, S-metolachlor, dimethenamide, dimethenamide-P or flufenacet.
4. Treatment of weeds in wheat post-emergent with Safener (I), such as (Ia) or (Ib), in combination with S-metolachlor.
5. Treatment of weeds in barley post-emergent with Safener (I), such as (Ia) or (Ib), in combination with S-metolachlor.

The following-herbicide safener combinations are preferred:
(B1-1)+(Ia); (B1-2)+(Ia); (B2-1)+(Ia); (B2-2)+(Ia); (B2-3)+(Ia); (B2-4)+(Ia);
(B3-1)+(Ia); (B4-1)+(Ia); (B5-1)+(Ia); (B5-2)+(Ia); (B5-3)+(Ia); (B5-4)+(Ia);
(B1-1)+(Ib); (B1-2)+(Ib); (B2-1)+(Ib); (B2-2)+(Ib); (B2-3)+(Ib); (B2-4)+(Ib);
(B3-1)+(Ib); (B4-1)+(Ib); (B5-1)+(Ib); (B5-2)+(Ib); (B5-3)+(Ib); (B5-4)+(Ib);

Also preferred are the combinations
(B1-1)+(B1-2) (Ia); (B2-1)+(B2-2)+(Ia); (B2-1)+(B2-3)+(Ia); (B2-1)+(B2-4)+(Ia); (B2-2)+(B2-3)+(Ia); (B2-2)+(B2-4)+(Ia); (B2-3)+(B2-4)+(Ia);
(B1-1)+(B1-2) (Ib); (B2-1)+(B2-2)+(Ib); (B2-1)+(B2-3)+(Ib); (B2-1)+(B2-4)+(Ib); (B2-2)+(B2-3)+(Ib); (B2-2)+(B2-4)+(Ib); (B2-3)+(B2-4)+(Ib).

The amount of antidote used in the method of the invention varies according to a number of parameters including the particular safener employed, the crop to be protected, the amount and rate of pesticide applied, the soil type and climatic conditions prevailing. Also, the selection of the specific safener for use in the method of the invention, the manner in which it is to be applied and the determination of the activity which is non-phytotoxic but antidotally effective, can be readily performed in accordance with common practice in the art.

The application rate of safener can vary within wide limits and is for example from 0.001 to 10 kg a.i. safener/ha.

The application rate of the herbicides (B) are in the range used for the herbicides alone and are thus known per se; see e. g. said "The Pesticide Manual".

The weight ratio of safener to pesticide can be varied within wide limits, and its optimum weight ratio depends both on the active, compounds safener and pesticide employed and on the kind of useful plants to be protected. The required safener application rate, depending on the pesticide employed and the kind of useful plant to be protected, can be determined by preliminary tests.

The ratio by weight of safener to herbicide is for example 50:1 to 1:50, preferably 20:1 to 1:20, in particular 10:1 to 1:10. In the case of a seed treatment the application rate of safener is from 0.01 to 10 grammes safener a.i. per kilogramme seed, preferably 0.05 to 1 g a.i. safener per kg seed, in particular 0.1 to 0.5 g a.i. safener per kilogramme seed, preferably corn seed.

If solutions of safeners are used in the seed treatment method wherein the seeds are soaked in the safener solution, the concentration of the safener in the solution is for example from 1 to 10000 ppm, preferably 100 to 1000 ppm based on weight.

The antidote is applied in a non-phytotoxic antidotally effective amount. By "non-phytotoxic" is meant an amount of the antidote which causes at most minor or no injury to the desired crop species. By "antidotally-effective" is meant an antidote (safener) used in an amount which is effective as an antidote with the herbicide to decrease the extent of injury caused by the herbicide to the desired crop species.

The method of the invention may be used to obtain selective weed control with low crop injury in various crop plants such as maize, cereals such as wheat, barley and rye, oats, rice, soybean, cotton, canola, sugar beet, potatoes, tobacco, and oil seed rape. Preferred crops include maize, rice arid cereals, sugar beet, cotton and canola. Particularly preferred crop species are maize, wheat, barley, rice, soybean and cotton Preferred crops of useful plants are cereals and maize, especially maize (corn).

The safener may also be used in crops of genetically engineered plants which are either known or still to be developed. As a rule, the transgenic plants are distinguished by particular, advantageous properties, for example by resistances to certain crop protection agents, resistances to plant diseases or pathogens causing plant diseases such as particular insects or microorganisms such as fungi, bacteria or viruses. Other particular properties relate for example, to the harvested material in terms of quantity, quality, storing properties, composition and specific constituents. Thus, transgenic plants are known which have an increased starch content or an altered starch quality, or those where the harvested material has a different fatty acid composition.

The safeners may be used in economically important transgenic crops of useful plants and ornamentals, for example cereals such as wheat, barley, rye, oats, panic grasses, rice, cassava and corn or else crops of sugar beet, cotton, soya, oilseed rape, potatoes, tomatoes, peas and other types of vegetables.

Particularly preferred are maize (corn) varieties. Examples for possible corn varieties are:

CARGILL 1077, 814–46 (POPCORN), 8527 (WHITE), 8540LLI, 8540LLI, BECKS 5305, BECKS 5405, CARGILL 7050LL, CIBA 454, COUNTER, DEKALB 546, DEKALB 592SR, DEKALB 614, DEKALB 623, DEKALB 626, DEKALB 642, DEKALB 674, DEKALB 689, FORCE, G 8541, GC 8101, GC8101, GC8101, H013, H037, H131, H132, H139, H626, HLIB, HOLDEN 1205410, HOLDEN 1310112, HOLDEN 1310113, HOLDEN 1325001, HOLDEN 1325023, HOLDEN 1397528, HOLDEN LL, HOLDENS 1196637, HOLDENS 1205402, HOLDENS 1310113, HOLDENS LL 19962.18, HYPERFORMER 9843, ICI 8539, ICI 8541, ICI 8801, IL XTRA (SWEET), IXLXSWT, LIBERTY LINK, NORTHRUP KING 2555BT, NORTHRUP KING 3030BT, NORTHRUP KING 4218, NORTHRUP KING 4242, NORTHRUP KING 4242+CNTR, NORTHRUP KING 4242BT, NORTHRUP KING 4620, NORTHRUP KING 6800BT, NORTHRUP KING 7070, NORTHRUP KING 7639B, NORTHRUP KING 8811, P3394/COUNTER @ 12 oz, P3394/COUNTER @ 6 oz, P3394/FORCE, PIONEER 3049*, PIONEER 3082, PIONEER 3085, PIONEER 3140, PIONEER 3163, PIONEER 3165, PIONEER 3335, PIONEER 3394, PIONEER 3395IR, PIONEER 33A63, PIONEER 33G28, PIONEER 33K81, PIONEER 33Y11, PIONEER 3489, PIONEER 34A55, PIONEER 34A55LL, PIONEER 34B25, PIONEER 34P93, PIONEER 34T14, PIONEER 35N05, PIONEER 3677, PIONEER 3751, PIONEER 3751IR, PIONEER 37H97, PIONEER 37R71, PIONEER 3893, PIONEER 3897, PIONEER 38B22LL, PIONEER 3936, PIONEER 3941, PIONEER 3963, PIONEER 3984, TERRA 1167 and WYFFEL 794

The method of using safeners of the formula (I) have a particular advantage in combination with the application of herbicides which cause considerable damage to useful plants. The combinations exhibit a resonable low phytotoxicity and good selectivity which is not found in the same manner with other herbicide-safener combinations.

The safeners of the formula I as well as the herbicides can be formulated in the usual manner various ways, depending on the prevailing chemical-physical and biological parameters. Examples of suitable formulations fare.

emulsifiable concentrates which are prepared by dissolving the active compounds in an organic solvent, example butanol, cyclohexanone, dimethylformamide, xylene or else higher-boiling hydrocarbons or mixtures of the organic solvents with addition of one or more ionic and/or nonionic surfactants (emulsifiers). Suitable emulsifiers are, for example, calcium alkylarylsulfonates, fatty acid polyglycol esters, alkylaryl polyglycol ethers, fatty alcohol polyglycol ethers, propylene oxide/ethylene oxide condensates, alkyl polyethers, sorbitan esters and polyoxyethylenesorbitan fatty acid esters dusts, which are obtained by grinding the active compounds with finely dispersed solid inorganic or organic substances, for example talc, natural clays, such as kaolin, bentonite and pyrophyllite, diatomaceous earth or meals water- or oil-based suspension concentrates, which can be prepared, for example, by wet grinding using bead mills water-soluble powders water-soluble concentrates granules, such as water-soluble granules, water-dispersible granules and granules for application by broadcasting and soil application wettable powders, which, in addition to active compound, also contain diluents or inert substances and surfactants capsule suspensions and microcapsules ultra-low-volume formulations.

The abovementioned formulation types are known to the person skilled in the art and described, for example, in: K. Martens, "Spray Drying Handbook", 3rd Ed., G. Goodwin Ltd., London. 1979; W. van Valkenburg, "Pesticide Formulations", Marcel Dekker, N.Y. 1973; Winnaker-Küchler, "Chemische Technologie" [Chemical Technology], Volume 7, C. Hauser Verlag Munich, 4th Edition 1986; "Perry's Chemical Engineer's Handbook", 5th Ed., McGraw-Hill, N.Y. 1973, pages 8–57.

The formulation auxiliaries required, such as inert materials, surfactants, solvents and further additives are also known and are described, for example, in: McCutcheon's "Detergents and Emulsifiers Annual", MC Publ. Corp., Ridgewood N.J.; C. Marsden, "Solvents Guide", 2nd Ed., Interscience, N.Y. 1963; H. von Olphen, "Introduction to Clay Colloid Chemistry", 2nd Ed., J. Wiley & Sons, N.Y.; Schönfeldt, "Grenzflächenaktive Äthylenoxidaddukte" [Surface-Active Ethylene Oxide Adducts], Wiss. Verlagsgesellschaft, Stuttgart 1976; Sisley and Wood, "Encyclopedia of Surface Active Agents", Chem. Publ. Co. Inc., N.Y. 1964; Watkins, "Handbook of Insecticide Dust Diluents and Carriers", 2nd Ed., Darland Books, Caldwell N.J.; Winnacker-Küchler, "Chemische Technologie", Volume 7, C. Hauser Verlag Munich, 4th Edition 1986.

In addition to the abovementioned formulation auxiliaries, the crop protection formulations compositions may comprise, if appropriate, customary tackifiers, wetting agents, dispersants, penetrants, emulsifiers, preservatives, antifreeze agents, fillers, carriers, colorants, anti-foams, evaporation inhibitors and pH and viscosity regulators.

Depending on the formulation type, the crop protection compositions generally comprise 0.1 to 99% by weight, in particular 0.2 to 95% by weight, of one or more safeners of the formula I or a combination of safener and pesticide. Furthermore, they comprise 1 to 99.9, in particular 4 to 99.5, % by weight of one or more solid or liquid additives and 0 to 25, in particular 0.1 to 25, % by weight of a surfactant. In emulsifiable concentrates, the active compound concentration, i.e. the concentration of safener and/or pesticide, is generally 1 to 90, in particular 5 to 80, % by weight. Dusts usually comprise 1 to 30, preferably 5 to 20, % by weight of active compound. In wettable powders, the active compound concentration is generally 10 to 90% by weight. In water-dispersible granules, the active compound content is, for example between 1 and 95% by weight, preferably between 10 and 80% by weight.

For use, the formulations which are present in commercial form are, if appropriate, diluted in a customary manner, for example in the case of wettable powders, emulsifiable concentrates, dispersions and water-dispersible granules with water. Dust preparations, granules and sprayable solutions are usually not diluted with any further inert substances prior to use. The required rate of application of the safeners varies with the external conditions such as, inter alia, temperature, humidity, and the kind of herbicide employed.

The safeners (I) and herbicides are usually formulated and in most cases then diluted with water for the purposed of providing a ready-to-use formulation or spray-formulation to be applied to the soil, plants or the area under cultivation.

The following non-limiting examples illustrate the invention wherein safener (Ia) is 5,5-diphenylisoxazoline-3-carboxylic acid and safener (Ib) is ethyl 5,5-diphenylisoxazoline -3-carboxylate.

1. FORMULATION EXAMPLES

1.1 Dusting Agents

A dusting agent is obtained by mixing 10 parts by weight of a compound of the formula I or of an active compound mixture of a herbicide and a safener of the formula I and 90 parts by weight of talc as inert material and comminuting in a hammer mill.

1.2 Water-Dispersible Powder

A wettable powder which is readily dispersible in water is obtained by mixing 25 parts by weight of a compound of the formula I or of an active compound mixture of a herbicide and a safener of the formula I, 64 parts by weight of kaolin-containing quartz as inert material, 10 parts by weight of potassium ligninsulfonate and 1 part by weight of sodium oleoylmethyltaurinate as wetting and dispersing agent, and grinding in a pin mill.

1.3 Water-Dispersible Concentrate

A dispersion concentrate which is readily dispersible in water is obtained by mixing 20 parts by weight of a compound of the formula I or of an active compound mixture of a herbicide and a safener of the formula I with 6 parts by weight of alkylphenol polyglycol ether (®Triton X 207), 3 parts by weight of isotridecanol polyglycol ether and 71 parts by weight of paraffinic mineral oil and grinding in a ball mill to a fineness of below 5 microns.

1.4 Emulsifiable Concentrate

An emulsifiable concentrate is obtained from 15 parts by weight of a compound of the formula I or of an active compound mixture of a herbicide and a safener of the formula I, 75 parts by weight of cyclohexanone as solvent and 10 parts by weight of ethoxylated nonylphenol as emulsifier.

1.5 Water-Dispersible Granules

Water dispersible granules are obtained by mixing

| 75 | parts by weight | of a safener of the formula I or of a mixture of a pesticide and a safener of the formula I, |
|---|---|---|
| 10 | " | of calcium ligninsulfonate, |
| 5 | " | of sodium lauryl sulfate, |
| 3 | " | of polyvinyl alcohol and |
| 7 | " | of kaolin, | grinding in a pin mill and granulating the powder in a fluidized bed by spraying on water as granulation liquid.

| Water-dispersible granules are also obtained by homogenizing | | |
|---|---|---|
| 25 | parts by weight | of a safener of the formula I or of a mixture of a pesticide and a safener of the formula I, |
| 5 | " | of sodium 2,2'-dinaphthylmethane-6,6'-disulfonate, |
| 2 | " | of sodium oleoylmethyltaurinate, |
| 17 | " | of calcium carbonate, |
| 50 | " | of water and |
| 1 | part by weight | of polyvinyl alcohol | in a colloid mill, comminuting, then grinding in a bead mill and atomizing and drying the resulting suspension in a spray tower using a single-fluid nozzle.

3 BIOLOGICAL EXAMPLES

3.1 Scoring of the Damage

The damage to the plants is assessed visually on a scale of 0–100% in comparison with control plants:

0%=no noticeable effect in comparison with the untreated plant

100%=the treated plant dies off.

3.2 Effect of the Herbicide and Effect of the Safener when Applied Pre-Emergence Seeds or rhizome pieces of mono- and dicotyledonous harmful plants and of crop plants are placed in sandy loam soil in plastic pots of a diameter of 9 cm and covered with soil. Alternatively, harmful plants encountered in paddy rice cultivation are cultivated in water-saturated soil, where the amount of water poured into the pots is such that the water level is at the soil surface, or some millimeters above the soil surface. The herbicide/safener active compound combinations according to the invention, formulated in the form of emulsion concentrates, and, in parallel tests, the correspondingly formulated individual active compounds are then applied as emulsions to the surface of the soil cover in various dosages using an amount of water of 300 l/ha (converted), or, in the case of rice, are poured into the irrigation water. After the treatment, the pots are placed in a greenhouse and kept under good growth conditions for the weeds. Visual scoring of the damage to the plants or the emerging plants was carried out in comparison with untreated controls after the test plants had emerged after a test period of 2–3 weeks.

Some tests show good herbicidal pre-emergence activity against a broad spectrum of broad-leaved weeds and weed grasses, and damage to crop plants such as maize, rice, wheat or barley or other cereals is considerably reduced in comparison with application of individual herbicides without safener.

3.3 Effect of the Herbicide and Effect of the Safener When Applied Post-Emergence Seeds or rhizome pieces of mono- and dicotyledenous harmful plants and of crop plants are placed in sandy loam soil in plastic pots, covered with soil and cultivated in a greenhouse under good growth conditions. Alternatively, harmful plants encountered in paddy rice cultivation are cultivated in pots where the water level is up to 2 cm above the soil surface. Three weeks after sowing, the test plants are treated at the three-leaf stage. The herbicide/safener active compound combinations according to the invention, formulated as emulsion concentrates, and, in parallel tests, the correspondingly formulated individual active compounds are sprayed onto the green parts of the plants in various dosages using an amount of water of 300 l/ha (converted) and, after the test plants have been kept in the greenhouse for 2–3 weeks under optimum growth conditions, the effect of the preparations is scored visually in comparison to untreated controls. In the case of rice or of harmful plants encountered in rice cultivation, the active compounds are also added directly to the irrigation water (application similar to granules application) or sprayed onto plants and into the irrigation water. Some tests show good herbicidal post-emergence activity against a broad spectrum of broad-leaved weeds and weed grasses, and damage to crop plants such as maize, rice, wheat or barley or other cereals is considerably reduced in comparison with application of individual herbicides without safener.

3.4 Seed Treatment

The number of crop seeds that would be needed for each safener rate was calculated. Based on the weight of 100 seeds, sufficient seeds were weighed into screw top glass bottles approximately twice the volume of the seeds.

The prospective safeners were formulated as wettable powders or water dispersible granules. These formulations were weighed out so that the required rates (g a.i./kg seed) would be obtained. The samples were added to the seeds in the bottles and then sufficient water added to produce a slurry. The bottles were capped and then placed in an overhead shaker (set at medium speed for up to 1 hour) so that the seeds were evenly coated with the slurry. The bottles were uncapped and the seeds used in the pre- or post-emergence tests as described in sections 3.5 and 3.6.

As an alternative seed treatment method, active ingredient of the prospective safeners was weighed and dissolved in a solvent (e.g. acetone) and added to the seeds in the bottles. The solvent type and volume was selected based on prior experience so that it would have no negative impact on seed germination or subsequent plant growth. After shaking for up to 1 hour (overhead shaker) the seeds were spread out on paper in a fume cabinet to allow the remaining solvent to evaporate. The seeds were then used in the pre- or post-emergence tests as described in sections 3.5 and 3.6.

In tests in which larger quantities of seeds required treatment, the prospective safeners, either as formulated samples in water or as active ingredient dissolved in solvent were applied to seeds using a mini-rotostat apparatus. The seeds were allowed to dry for a short time before being used in the pre- or post-emergence tests as described in sections 3.5 and 3.6.

3.5 Pre-Emergence Herbicide Application

The safener treated seeds and untreated comparison seeds were sown into 7 to 13 cm round pots in a sandy loam soil and covered with approximately 0.5 to 1 cm of a 1 to 1 mix of sandy loam soil and sand. Herbicidal substances, as liquid (e.g. Emulsifiable concentrates) or dry (e.g. wettable powder) formulations, were diluted to the required concentrations in deionised water and applied to the soil surface using a track sprayer calibrated to deliver 300 to 800 litres of spray solution per hectare.

The pots were placed under good growing conditions in a glasshouse and a visual assessment of herbicidal effects made after 3 to 4 weeks after herbicide application. Assessment was on a percentage basis in comparison with untreated control plants (0%=no injury, 100%=complete kill).

3.6 Post-Emergence Herbicide Application

The safener treated seeds and untreated comparison seeds were sown into 9 to 13 cm round pots in a sandy loam soil and covered with approximately 1 cm of a 1 to 1 mix of sandy loam soil and sand. The pots were placed under good growing conditions in a glasshouse for approximately 2–3 weeks, until the plants reached the 2 to 4 leaf stage. Herbicidal substances, as liquid (e.g. Emulsifiable concentrates) or dry (e.g. wettable powder) formulations, were diluted to the required concentrations in deionised water and applied to the green plant parts and intervening soil surface using a track sprayer calibrated to deliver 300 to 800 litres of spray solution per hectare.

The pots were returned under good growing conditions in a glasshouse and a visual assessment of herbicidal effects made at intervals from 1 to 4 weeks after herbicide application. Assessment was on a percentage basis in comparison with untreated control plants (0%=no injury, 100%=complete kill).

3.7 Specific Examples for Post-Emergence Treatment

In a series of trials the ability of herbicides to be safened by safener (Ib) was evaluated. The results are summarized in Tables 1.

TABLE 1

| Active ingredients | Application rate g a. i./ha | % injury to ZEAMA |
|---|---|---|
| (B1-1) | 10 | 18 |
| (B1-1) + (Ib) | 10 + 60 | 10 |
| (B1-2) | 30 | 32 |
| (B1-2) + (Ib) | 30 + 30 | 15 |
| (B2-1) + (B2-2) | (288 + 112) | 21 |
| (B2-1) + (B2-2) + (Ib) | (288 + 112) + 30 | 6 |
| (B2-3) | 420 | 22 |

TABLE 1-continued

| Active ingredients | Application rate g a. i./ha | % injury to ZEAMA |
|---|---|---|
| (B2-3) + (Ib) | 420 + 100 | 11 |
| (B2-4) | 160 | 9 |
| (B2-4) + (Ib) | 160 + 50 | 5 |
| (B3-1) | 560 | 23 |
| (B3-1) + (Ib) | 560 + 100 | 17 |
| (B4-1) | 36 | 11 |
| (B4-1) + (Ib) | 36 + 100 | 8 |

Abbreviations:
B-No. = numbers of herbicides (B) as defined in the specification above
Safener (Ib) = ethyl 5,5-diphenyl-2-isoxazoline-3-carboxylate
ZEAMA = *Zea mays* (maize)

3.8 Pre-Emergence Application with Herbicide Safener Combination

Wheat or barley were treated according to example 3.2. The results are summarised in Tables 2 and 3.

TABLE 2

| Active ingredients | Application rate g a. i./ha | % injury to TRZAS |
|---|---|---|
| (B5-1) | 300 | 70 |
| (B5-1) + (Ib) | 300 + 300 | 10 |
| (B5-1) + (Ia) | 300 + 300 | 20 |

TABLE 3

| Active ingredients | Application rate g a. i./ha | % injury to HORVS |
|---|---|---|
| (B5-1) | 300 | 15 |
| (B5-1) + (Ib) | 300 | 0 |

Abbreviations in Tables 2 and 3:
B-No. = numbers of herbicides (B) as defined in the specification above
Safener (Ib) = ethyl 5,5-diphenyl-2-isoxazoline-3-carboxylate
TRAZAS = *Triticum aestivum* (wheat)
HORVS = *Hordeum vulgare* (barley)

3.9 Post-Emergence Application with Herbicide Safener Combination

Corn was grown until the 2 to 3-leaf stage. Then the herbicide or the herbicide-safener combination, respectively, defined in Table 4 was applied post-emergent as described in example 3.3. After 3 to 4 weeks the results were visually scored in comparison with control plants (without safener and herbicide treatment). The results are summarised in Table 4 below.

TABLE 4

| Active ingredients | Application rate g a. i./ha | % injury to corn (variety Lorenzo) | % injury to corn (variety Dea) |
|---|---|---|---|
| (B2-1) + (B2-2) | (550 + 214) | 18 | 30 |
| (B2-1) + (B2-2) + (Ib) | (550 + 214) + 200 | 5 | 5 |

Abbreviations in Tables 2 and 3:
B-No. = numbers of herbicides (B) as defined in the specification above;
(B2-1) + (B2-2) specifically is a herbicidal composition containing 55% sodium salt of dicamba and 21.4% sodium salt of diflufenzopyr
Safener (Ib) = ethyl 5,5-diphenyl-2-isoxazoline-3-carboxylate

What is claimed is:
1. A herbicide safener combination comprising
   A) an effective amount of a compound of the formula (I) or a salt thereof,

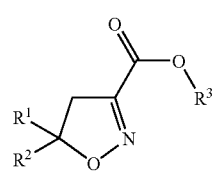

in which
R$^1$ is phenyl which is unsubstituted or substituted,
R$^2$ is (C$_1$–C$_6$)alkyl, (C$_3$–C$_6$)cycloalkyl or phenyl, each of the 3 last-mentioned radicals is unsubstituted or substituted,
R$^3$ is hydrogen or a hydrocarbon radical having 1 to 18 C-atoms which is unsubstituted or substituted,
and
   B) a herbicide selected from the group consisting of
   (B1) Triazolopyrimidine derivatives (B1-1) and (B 1-2)
      (B1-1) N-(2,6-difluorophenyl)-8-fluoro-5-methoxy-1,2,4triazolo[1,5-c]pyrimidin-2-sulfonamide (florasulam),
      (B-1-2) methyl 3-chloro-(5-ethoxy-7-fluoro[1,2,4]triazole-[1,5-c]pyrimidin-2-ylsulfonamido)-benzoate (cloransulam)
   (B2) plant hormone-type herbicides (B2-1) to (B2-4)
      (B2-1) 3,6-dichloro-2-methoxy-benzoic acid and salts and esters thereof; (dicamba),
      (B2-2) 2-{1-[4-(3,5-difluorophenyl)semicarbazono]ethyl}nicotinic acid and salts thereof (diflufenzopyr);
      (B2-3) 3,5,6-trichloro-2-pyridyloxyacetic acid (triclopyr);
      (B2-4) 4-amino-3,5-dichloro-6-fluoro-2-pyridyloxyacetic acid and salts and esters thereof (fluroxypyr); and
   (B3-1) 4-amino-6-tert-butyl-4,5-dihydro-3-methylthio-1,2,4-triazin-5-one (metribuzin);
   (B4-1) ethyl (RS)-2-chloro-3-[2-chloro-5-(4-difluoromethyl-4,5-dihydro-3-methyl-5-oxo-1H-1,2,4-triazol-1-yl)-4-fluorophenyl]propionate (carfentrazone-ethyl)
   (B5) chloroacetanilides (B5-1) to (B5-4)
      (B5-1) 2-chloro-N-(2-ethyl-6-methylphenyl)-N-[( 1 S)-2-methoxy-1-methylethyl)]-acetamide (S-metolachlor),
      (B5-2) (RS)-2-chloro-N-(2,4-diethyl-3-thienyl)-N-(2-methoxy-1-methylethyl)acetamide (dimethenamid),
      (B5-3) (S)-2-chloro-N-(2,4-diethyl-3-thienyl)-N-(2-methoxy-1-methylethyl)acetamide (dimethenamid-P), and
      (B5-4) 4'-fluoro-N-isopropyl-2-[5-trifluoromethyl-1,3,4-thiadiazol-2-yloxy]acetanilide (flufenacet) and
mixtures of the above herbicides, optionally in combination with other herbicidal active ingredients.
2. A combination as claimed in claim 1 wherein in formula (I)
R$^1$ is phenyl which is unsubstituted or substituted by one or more radicals selected from the group consisting of halogen, cyano, nitro, amino, $(C_1-C_4)$haloalkyl, $(C_1-C_4)$haloalkoxy, $(C_1-C_4)$alkyl, $(C_1-C_4)$alkoxy, mono$(C_1-C_4)$alkyl-amino, di$(C_1-C_4)$alkyl-amino, $(C_1-C_4)$alkylthio and $(C_1-C_4)$alkylsulfonyl, $R^2$ is $(C_1-C_6)$alkyl, $(C_3-C_6)$cycloalkyl or phenyl, each of the 3 last-mentioned radicals is unsubstituted or substituted by one or more radicals selected from the group consisting of halogen, cyano, nitro, amino, $(C_1-C_4)$haloalkyl, $(C_1-C_4)$haloalkoxy, $(C_1-C_4)$alkyl, $(C_1-C_4)$alkoxy, mono$(C_1-C_4)$alkyl-amino, di$(C_1-C_4)$alkyl-amino, $(C_1-C_4)$alkylthio and $(C_1-C_4)$alkylsulfonyl, $R^3$ is hydrogen or a hydrocarbon radical having 1 to 18 C-atoms which is unsubstituted or substituted by one or more radicals selected from the group consisting of halogen, cyano, thio, nitro, hydroxyl, $(C_1-C_6)$alkyl, $(C_1-C_6)$haloalkyl, the 2 last-mentioned radicals as substituents of cyclic radicals only, $(C_1-C_6)$alkoxy, $(C_2-C_6)$alkenyloxy, $(C_2-C_6)$alkinyloxy, $(C_1-C_6)$haloalkoxy, $(C_2-C_6)$alkylthio, $(C_3-C_6)$cycloalkyl, $(C_3-C_6)$cycloalkoxy, $(C_1-C_8)$alkoxy-carbonyl, $(C_2-C_6)$alkenyloxy-carbonyl, $(C_2-C_6)$alkinyloxy-carbonyl, $(C_1-C_8)$alkyl-carbonyl, $(C_1-C_6)$alkyl-carbonyloxy, phenyl, phenyl-$(C_1-C_6)$alkoxy, phenyl-$(C_1-C_6)$alkoxy-carbonyl, phenoxy, phenoxy-$(C_1-C_6)$alkoxy, phenoxy-$(C_1-C_6)$alkoxy-carbonyl, phenoxycarbonyl, phenylcarbonyloxy and phenyl-$(C_1-C_6)$alkyl-carbonyloxy, wherein the 9 last-mentioned radicals are unsubstituted or substituted in the phenyl ring by one or more radicals selected from the group consisting of halogen, $(C_1-C_4)$alkyl, $(C_1-C_4)$alkoxy, $(C_1-C_4)$haloalkyl, $(C_1-C_4)$haloalkoxy and nitro, and radicals of the formula —O—N=CR'$_2$, —N=CR'$_2$, wherein the R' in the formulae independently of one another are hydrogen, $(C_1-C_4)$alkyl or phenyl, which is unsubstituted or substituted by one or more radicals selected from the group consisting of halogen, $(C_1-C_4)$alkyl, $(C_1-C_4)$alkoxy, $(C_1-C_4)$haloalkyl, $(C_1-C_4)$haloalkoxy and nitro, or together are a $(C_2-C_6)$alkylene chain.

3. The combination claimed in claim 2 wherein in formula (I)

$R^1$ and $R_2$ both are phenyl and $R^3$ is hydrogen or $(C_1-C_6)$alkyl which is unsubstituted or substituted by one or more radicals selected from the group consisting of
halogen, cyano, $(C_1-C_4)$alkoxy, $(C_2-C_4)$alkenyloxy, $(C_2-C_4)$alkinyloxy, $(C_1-C_4)$haloalkoxy, $(C_2-C_4)$alkylthio, $(C_3-C_6)$cycloalkyl, $(C_3-C_6)$cycloalkoxy, $(C_1-C_4)$alkoxy-carbonyl, $(C_2-C_4)$alkenyloxy-carbonyl, $(C_2-C_4)$alkinyloxy-carbonyl, $(C_1-C_4)$alkyl-carbonyl, $(C_1-C_4)$alkyl-carbonyloxy, phenyl which is unsubstituted or substituted in the phenyl ring by one or more radicals selected from the group consisting of halogen, $(C_1-C_4)$alkyl, $(C_1-C_4)$alkoxy, $(C_1-C_4)$haloalkyl and $(C_1-C_4)$haloalkoxy.

4. The combination as claimed in to claim 3 wherein in formula (I)
$R^3$ is H or $(C_1-C_4)$alkyl.

5. The combination as claimed in claim 1 wherein the safener of formula (I) is 5,5-diphenyl-2-isoxazoline-3-carboxylic acid.

6. The combination as claimed in claim 5, wherein the herbicide is selected from the group consisting of:
(B1-1) florasulam;
(B1-2) cloransulam;
combination of (B2-1) dicamba and (B2-2) diflufenzopyr;
(B2-3) triclopyr;
(B2-4) fluroxypyr;
(B3-1) metribuzin;
(B4-1) carfentrazone-methyl;
(B5-1) S-metolachlor;
(B5-2) dimethenamid;
(B5-3) dimethenamid-P;
(B5-4) flufenacet; and
mixtures thereof.

7. A method of combatting weed plants in a crop of useful plants wherein a safener A) is applied to the plants, seed of the plants or the area under cultivation before, simultaneously or after a herbicide A) pre-emergent and/or post-emergent related to the crop and wherein the safener A) and the herbicide B) are as defined in claim 6.

8. A method of reducing the phytotoxicity of a herbicide B) to a crop plant wherein a safener A) is applied to the plants, seed of the plants or the area under cultivation before, simultaneously or after a herbicide A) pre-emergent and/or post-emergent related to the crop and wherein the safener A) and the herbicide B) are as defined in claim 6.

9. A method of combatting weed plants in a crop of useful plants wherein a safener A) is applied to the plants, seed of the plants or the area under cultivation before, simultaneously or after a herbicide A) pre-emergent and/or post-emergent related to the crop and wherein the safener A) and the herbicide B) are as defined in claim 5.

10. A method of reducing the phytotoxicity of a herbicide B) to a crop plant wherein a safener A) is applied to the plants, seed of the plants or the area under cultivation before, simultaneously or after a herbicide A) pre-emergent and/or post-emergent related to the crop and wherein the safener A) and the herbicide B) are as defined in claim 5.

11. The combination as claimed in claim 1 wherein the safener of formula (I) is ethyl 5,5-diphenyl-2-isoxazoline-3-carboxylate.

12. The combination as claimed in claim 11, wherein the herbicide is selected from the group consisting of:
(B1-1) florasulam;
(B1-2) cloransulam;
combination of (B2-1) dicamba and (B2-2) diflufenzopyr;
(B2-3) triclopyr;
(B2-4) fluroxypyr;
(B3-1) metribuzin;
(B4-1) carfentrazone-methyl;
(B5-1) S-metolachlor;
(B5-2) dimethenamid;
(B5-3) dimethenamid-P;
(B5-4) flufenacet; and
mixtures thereof.

13. A method of combatting weed plants in a crop of useful plants wherein a safener A) is applied to the plants, seed of the plants or the area under cultivation before, simultaneously or after a herbicide A) pre-emergent and/or post-emergent related to the crop and wherein the safener A) and the herbicide B) are as defined in claim 12.

14. A method of reducing the phytotoxicity of a herbicide B) to a crop plant wherein a safener A) is applied to the plants, seed of the plants or the area under cultivation before, simultaneously or after a herbicide A) pre-emergent and/or post-emergent related to the crop and wherein the safener A) and the herbicide B) are as defined in claim 12.

15. A method of combatting weed plants in a crop of useful plants wherein a safener A) is applied to the plants, seed of the plants or the area under cultivation before, simultaneously or after a herbicide A) pre-emergent and/or post-emergent related to the crop and wherein the safener A) and the herbicide B) are as defined in claim 11.

16. A method of reducing the phytotoxicity of a herbicide B) to a crop plant wherein a safener A) is applied to the plants, seed of the plants or the area under cultivation before, simultaneously or after a herbicide A) pre-emergent and/or post-emergent related to the crop and wherein the safener A) and the herbicide B) are as defined in claim 11.

17. The combination as claimed in claim 1 which is a co-formulation additionally containing formulation auxiliaries.

18. The combination as claimed in claim 1, wherein the herbicide is selected from the group consisting of:
(B1-1) florasulam;
(B1-2) cloransulam;
combination of (B2-1) dicamba and (B2-2) diflufenzopyr;
(B2-3) triclopyr;
(B2-4) fluroxypyr;
(B3-1) metribuzin;
(B4-1) carfentrazone-methyl;
(B5-1) S-metolachlor;
(B5-2) dimethenamid;
(B5-3) dimethenamid-P;
(B5-4) flufenacet; and
mixtures thereof.

19. The combination as claimed in claim 1 wherein the safener A) is ethyl-2-isoxazoline-3-carboxylate and the herbicide B) is florasulam or chloranulam.

20. The combination as claimed in claim 1 wherein the safener A) is ethyl-2-isoxazoline-3-carboxylate and the herbicide B) is dicamba.

21. The combination as claimed in claim 1 wherein the safener A) is ethyl-2-isoxazoline-3-carboxylate and the herbicide B) is a combination of dicamba and diflufenzopyr.

22. The combination as claimed in claim 1 wherein the safener A) is ethyl-2-isoxazoline-3-carboxylate and the herbicide B) is triclopyr.

23. The combination as claimed in claim 1 wherein the safener A) is ethyl-2-isoxazoline-3-carboxylate and the herbicide B) is fluroxypyr.

24. The combination as claimed in claim 1 wherein the safener A) is ethyl-2-isoxazoline-3-carboxylate and the herbicide B) is metribuzin.

25. The combination as claimed in claim 1 wherein the safener A) is ethyl-2-isoxazoline-3-carboxylate and the herbicide B) is carfentrazone-ethyl.

26. The combination as claimed in claim 1 wherein the safener A) is ethyl-2-isoxazoline-3-carboxylate and the herbicide B) is S-metolachlor.

27. The combination as claimed in claim 1 wherein the safener A) is ethyl-2-isoxazoline-3-carboxylate and the herbicide B) is dimethenamide.

28. The combination as claimed in claim 1 wherein the safener A) is ethyl-2-isoxazoline-3-carboxylate and the herbicide B) is dimethenamide-P.

29. The combination as claimed in claim 1 wherein the safener A) is ethyl-2-isoxazoline-3-carboxylate and the herbicide B) is flufenacet.

30. A method of combatting weed plants in a crop of useful plants wherein a safener A) is applied to the plants, seed of the plants or the area under cultivation before, simultaneously or after a herbicide A) pre-emergent and/or post-emergent related to the crop and wherein the safener A) and the herbicide B) are as defined in claim 1.

31. A method of reducing the phytotoxicity of a herbicide B) to a crop plant wherein a safener A) is applied to the plants, seed of the plants or the area under cultivation before, simultaneously or after a herbicide A) pre-emergent and/or post-emergent related to the crop and wherein the safener A) and the herbicide B) are as defined in claim 1.

* * * * *